United States Patent [19]

Wolfbeis et al.

[11] Patent Number: 5,232,858
[45] Date of Patent: Aug. 3, 1993

[54] METHOD FOR QUANTITATIVE DETERMINATION OF AT LEAST ONE CHEMICAL PARAMETER OF A SAMPLE MEDIUM

[75] Inventors: Otto S. Wolfbeis; Marco J. Leiner, both of Graz, Austria

[73] Assignee: AVL Medical Instruments AG, Schaffhausen, Switzerland

[21] Appl. No.: 844,938

[22] Filed: Mar. 4, 1992

Related U.S. Application Data

[63] Continuation of Ser. No. 512,444, Apr. 23, 1990, abandoned.

[30] Foreign Application Priority Data

Apr. 25, 1989 [AT]  Austria .................................. 1000/89

[51] Int. Cl.$^5$ ....................... G01N 21/64; G01N 21/29
[52] U.S. Cl. .......................................... 436/77; 436/79; 436/80; 436/81; 436/144; 436/172
[58] Field of Search ....................... 436/77, 79, 80, 81, 436/144, 172

[56] References Cited

U.S. PATENT DOCUMENTS 4,367,072  1/1983  Vögtle et al. ........................ 436/501
4,521,511  1/1985  Stout ................................... 436/135

Primary Examiner—Jill A. Johnston
Attorney, Agent, or Firm—Watson, Cole, Grindle & Watson

[57] ABSTRACT

A method for the quantitative determination of one or more chemical parameters of a sample medium employs a fluorescent agent which is not responsive to the parameter to be determined and which has an excitation spectrum and an emission spectrum, and a closely adjacent chromogenic agent which responds to the parameter of the sample medium to be determined by a change in its absorption spectrum the emission spectrum of the fluorescent agent at least partically overlapping the absorption spectrum of the chromogenic agent. The absorption maximum of chromogenic agent is shifted in accordance with the parameter to be determined, causing a reduction of fluorescence decay time t in the fluorescent agent, thereby enabling quantitative determination of the chemical parameter with improved long-term stability and infrequent calibrations.

11 Claims, No Drawings

METHOD FOR QUANTITATIVE DETERMINATION OF AT LEAST ONE CHEMICAL PARAMETER OF A SAMPLE MEDIUM

CROSS REFERENCE TO RELATED APPLICATION

The present application is a continuation of application Ser. No. 512,444, filed Apr. 23, 1990, now abandoned.

BACKGROUND OF THE INVENTION

The present invention relates to a method for the quantitative determination of one or more chemical parameters of a sample medium wherein two substances are used that are closely adjacent to each other, i.e., a first substance in the form of a fluorescent agent with an excitation spectrum and an emission spectrum, this first substance not being responsive to the parameter to be determined, and a second substance in the form of an agent whose absorption spectrum is changed by the parameter of the sample medium to be determined, the emission spectrum of the fluorescent substance at least partially overlapping the absorption spectrum of the second substance.

DESCRIPTION OF THE PRIOR ART

Much progress has been achieved in recent years in determining physical or chemical parameters, especially in the measuring of substances contained in a sample medium by means of optical sensors. Such optical sensors (optodes) usually comprise an indicator which is applied to a solid substrate and is in contact with the sample. The change of at least one optical property of the indicator, which is effected by the parameter to be determined, is measured in an optical system comprising a light source, optical filters, possibly fiber-optical lightguides, and photodetectors.

There are absorption-optical, reflection-optical and fluorescence-optical sensors. In the variants known so far it is mainly the intensity of fluorescence that is used as a measuring parameter, the concentration [Q] of a substance Q quenching the fluorescence of the indicator being determined by the equation:

$$F_o/F = 1 + K_{sv}[Q] \quad (1)$$

In the above equation $F_o$ and $F$ stand for the fluorescence intensities of the indicator quenched by Q in the absence or presence of the quencher with a concentration [Q]. $K_{sv}$ is an indicator-specific constant.

In the above method according to EP-A 214 768 a technique is described for determining specific substances, in which a fluorescent substance (fluorescent agent) and an absorber substance are immobilized on a substrate in close spatial contact. The emission spectrum of the substance fluorescing upon excitation overlaps the absorption spectrum of the absorber substance. Whereas the fluorescent agent does not respond to the substance to be determined, the absorber substance will produce a response upon contact with the sample which will cause the degree of overlap of emission and absorption spectrum to vary depending on the concentration of the substance to be determined. The change in fluorescence intensity obtained in this way is measured and used as a measure for the parameter to be determined.

The main disadvantages of intensity measurement are that the fluorescence intensity F is affected by fluctuations in the intensity of the excitation light source. Besides, F is dependent on the concentration of the fluorescent substance, whose fading will cause drifts. Finally, photodetectors may vary in sensitivity, which again will affect the measured intensity F.

In those instances in which the analytical variable acts as a dynamic quencher of the fluorescence of an indicator, the change in fluorescence decay time t may be used as a parameter, as according to Stern/Volmer the fluorescence decay time (t) in the presence and the fluorescence decay time ($t_o$) in the absence of a quencher of the concentration [Q], are related as follows:

$$t_o/t = 1 + K_{sv}[Q] \quad (2)$$

Dynamic quenchers are fluorescence quenchers quenching the fluorescence of a molecule by non-radiative inactivation of the excited state of a molecule, as a consequence of a dynamic collision process. This is in contrast to the static quencher whose effect is based on the fact that it forms a loose, non-fluorescing complex with the fluorescent substance in its ground state. The two quenching mechanisms have different effects on decay times; the dynamic quencher reducing decay time in accordance with equation (2), the static quencher not.

Typical sensors based on the measuring of decay time are described in DE 3 346 810 Al. The main advantage of measuring fluorescence decay time is that this method is much less error-prone than the one determining the concentration of the quencher Q by measuring fluorescence intensity, since the lifetime t of a fluorescent agent is independent of the intensity of the light source, the concentration of the dye and the sensitivity of the photodetector. Thus lifetime measurements are superior to intensity measurements even though they are technically more complex.

Known optical methods based on measuring decay time are only suitable for dynamic fluorescence quenchers, however, such as oxygen, $SO_2$ or halothanes. Lifetime measurements are not suitable for determining pH or other analytical parameters involving color changes in the presence of known indicators, as the color-forming reactions take place in the electronic ground state.

In this context the reader is referred to EP-A-0 242 527, which contains a description of a method of determining chemical analytes with the use of antigens or antibodies, i.e., special proteins capable of specifically binding the analyte. The described method is a so-called homogeneous immunoassay, i.e., a technique characterised by an antigen binding a specific antibody. The resulting bond will permit an energy transfer from a donor fluorescer bond to one ligand to an acceptor fluorescer bound to another ligand, as long as there is a spectral overlap and donor and acceptor are within the Förster radius.

SUMMARY OF THE INVENTION

It is an object of the present invention to develop the method referred to previously in such a way as to permit quantitative determination of parameters whose measuring by the advantageous method of decay time measurement has not been possible before.

In the invention this object is achieved by using as a second substance a chromogenic agent influencing the fluorescence of the fluorescent agent, the absorption maximum of the chromogenic substance shifting with the parameter to be determined, and by using the reduction in fluorescence decay time t occurring as a consequence of the energy transfer between chromogenic and fluorescent substance for quantitative determination of the chemical parameter. As an unexpected result of the energy transfer between chromogenic and fluorescent substance, a change in fluorescence decay time is found, which so far has only been observed in dynamic fluorescence quenching. This effect is employed for determining the parameters in the invention. The chromogenic and fluorescent substances are advantageously immobilized on a solid substrate.

In accordance with the width of the absorption band of the non-fluorescent chromogenic agent emission of the fluorescent agent will vary, resulting in a reduction of fluorescence decay time. It has been found unexpectedly that the measuring of decay times will also supply information on substances which do not act as dynamic quenchers of the fluorescence radiation of the fluorescent agent.

Thus the method described is characterized by a considerable improvement in long-term stability vis-a-vis conventional techniques, which will permit the use of measuring arrangements corresponding to the invention in measuring stations, avoiding frequent calibrations which have hitherto been necessary.

The theoretical basis of this effect is provided by the so-called energy transfer (ET), according to which electronic energy can be transferred from a donor (the fluorescent substance in this instance) to an acceptor (the analyte-sensitive chromogenic substance in this instance). There are no free photons in this process. The energy transfer is governed by the Förster equation $$k_{ET} = R_o^6/(r^6 t) \quad (3)$$

$k_{ET}$ being the velocity constant for ET, and $R_o$ and r, respectively, signifying the so-called critical distance and the actual distance, respectively, of donor and acceptor. $R_o$ (Förster radius) is that distance at which the probability of Förster ET is equal to that of spontaneous ET.

The efficiency of the energy transfer thus will depend on the quantum yield of the donor, the overlap of the emission spectrum of the acceptor, and their relative orientation and distance. Typical transfer distances are between 0.5 and 10 nm. The distance between donor and acceptor has considerable influence on the energy transfer, since the latter is dependent on the sixth power of this distance.

An application of the invention provides that for determining the hydrogen ion concentration 7-diethylamino-coumarin-3-carboxylic acid be used as a fluorescent substance, and methyl orange as a chromogenic substance, or rather, 8-aminopyrene-1,3,6-trisulphonate as a fluorescent substance and phenol red as a chromogenic substance.

Preferably, fluorescent substance (donor) and chromogenic substance (acceptor) are covalently attached to each other.

The subsequent table gives examples of combinations of a fluorescent and a chromogenic substance for determination of different chemical parameters, all fluorescent substances satisfying the demand that their fluorescence decay times must be within a measurable range.

| Fluorescent substance (donor) | Chromogenic substance (receptor) | Measuring wavelength (nm) | Chemical parameter |
|---|---|---|---|
| 7-diethylamino-coumarin-3-carboxylic acid | methyl orange | 480 | $H^+$ |
| 8-aminopyrene-1,3,6-trisulphonate | phenol red | 490 | $H^+$ |
| sulpho-rhodamine 101 | alizarin complexon | 590 | $Ba^{2+}$ |
| rhodamine 6G | beryllone | 570 | $Mg^{2+}$ |
| 2,7-dichloro-fluorescein | catechol violet | 540 | $Cd^{2+}$ |
| fluorescein | chrome azurol S | 520 | $Al^{3+}$ |
| coumarin 7 | eriochrome black T | 485 | $Ca^{2+}, Pb^{2+}$ |
| coumarin 343 | murexide | 450 | $Cu^{2+}$ |
| coumarin 334 | zincone | 440 | $Zn^{2+}$ |

We claim:

1. A method for the quantitative determination of at least one chemical parameter of a sample medium, comprising the steps of:
   (a) providing a fluorescent substance with an excitation spectrum and an emission spectrum and which displays a fluorescent decay time (t), said fluorescent substance being non-responsive to said chemical parameter to be determined;
   (b) providing a chromogenic substance having an absorption maximum which can be shifted in wavelength in accordance with said chemical parameter to be determined;
   (c) immobilizing said fluorescent and chromogenic substances in close vicinity to each other on a substrate so that the emission spectrum of said fluorescent substance at least partially overlaps the absorption spectrum of said chromogenic substance, influencing the fluorescence decay time of said fluorescent substance;
   (d) contacting said fluorescent and chromogenic substances with a sample medium defining at least one chemical parameter,
   (e) exposing said fluorescent substance to excitation radiation, and
   (f) measuring a reduction of said fluorescence decay time (t) caused by energy transfer between said chromogenic and said fluorescent substances for the quantitative determination of said chemical parameter.

2. A method according to claim 1, wherein said fluorescent substance is 7-diethylaminocoumarin-3-carboxylic acid, said chromogenic substance is methyl orange and said chemical parameter is hydrogen ion concentration.

3. A method according to claim 1, wherein said fluorescent substance is 8-aminopyrene-1,3,6-trisulphonate, said chromogenic substance is phenol red, and said chemical parameter is hydrogen ion concentration.

4. A method according to claim 1, wherein said fluorescent substance is sulphorhodamine 101, said chromogenic substance is alizarin-complexon, and said chemical parameter is barium ion concentration.

5. A method according to claim 1, wherein said fluorescent substance is rhodamine 6G, said chromogenic substance is beryllone, and said chemical parameter is magnesium ion concentration.

6. A method according to claim 1, wherein said fluorescent substance is 2,7-dichloro-fluorescein, said chromogenic substance is catechol violet, and said chemical parameter is cadmium ion concentration.

7. A method according to claim 1, wherein said fluorescent substance is fluorescein, said chromogenic substance is chrome azurol S, and said chemical parameter is aluminium ion concentration.

8. A method according to claim 1, wherein said fluorescent substance is coumarin 7, said chromogenic substance is eriochrome black T, and said chemical parameter is calcium or lead ion concentration.

9. A method according to claim 1, wherein said fluorescent substance is coumarin 343, said chromogenic substance is murexide, and said chemical parameter is copper ion concentration.

10. A method according to claim 1, wherein said fluorescent substance is coumarin 334, said chromogenic substance is zincone, and said chemical parameter is zinc ion concentration.

11. A method according to claim 1, wherein said fluorescent substance (donor) and said chromogenic substance (acceptor) are covalently attached to each other.

* * * * *